United States Patent [19]

Beck

[11] 4,284,623

[45] Aug. 18, 1981

[54] METHOD OF TREATING INFLAMMATION USING BOVINE MILK

[76] Inventor: Lee R. Beck, 2550 Dunmore Place, Birmingham, Ala. 35226

[21] Appl. No.: 92,957

[22] Filed: Nov. 9, 1979

[51] Int. Cl.$^3$ .......................................... A61K 39/395
[52] U.S. Cl. ..................................................... 424/85
[58] Field of Search ........................................ 424/85

[56] References Cited

U.S. PATENT DOCUMENTS

| | | | |
|---|---|---|---|
| 3,128,230 | 4/1964 | Heinbach | 424/85 |
| 3,376,198 | 4/1966 | Peterson et al. | 424/85 |
| 3,975,517 | 8/1976 | Wilson | 424/85 |

FOREIGN PATENT DOCUMENTS

| | | | |
|---|---|---|---|
| 53-26312 | 3/1978 | Japan | 424/85 |
| 1211876 | 11/1970 | United Kingdom | 424/85 |
| 1505513 | 3/1978 | United Kingdom | 424/85 |

OTHER PUBLICATIONS

Chemical Abstracts, vol. 89, *GENERAL SUBJECT INDEX* under *MILK*, pp. 1433GS to 1434GS (1978).
Misaka et al., Chem. Abstracts, vol. 89, abst. no. 30755e (1978) (abst. of Japan Kokai No. 78 26,312 pub. 03-11-78).
Derwent Japanese Abstracts 1978 ABSTRACT 29814 of Japanese Kokai No. 78-26,312).
Lascelles, vol. 25, Dairy Science Abstracts, pp. 359 to 364 (1963).
Holm, U.S. Patent Office Offical Gazette, Abstract of Applications, published Dec. 1950 (12-5-50), Abstract of Holm abandoned published application Ser. No. 628,937 filed 11151945.
The Merck Manual of Diagnosis and Therapy, Thirteenth Edition, (Merck and Co., Rahway, N.J. 1977), pp. 1321 to 1331 and 1339 to 1342.

*Primary Examiner*—John D. Randolph

[57] ABSTRACT

A method for treating inflammation in an animal which comprises administering to the animal an anti-inflammatory effective amount of milk collected from a bovid maintained in an anti-inflammatory factor producing state.

16 Claims, No Drawings

METHOD OF TREATING INFLAMMATION USING BOVINE MILK

BACKGROUND OF THE INVENTION

1. Field of the Invention

The present invention relates to anti-inflammatory milk, a process for its production and a method for its use in the treatment of inflammation.

2. Description of the Prior Art

Inflammation, as defined in Dorland's Medical Dictionary, is "a localized protective response elicited by injury or destruction of tissues which serves to destroy, dilute or wall off (squester) both the ingurious agent and the injured tissue. It is characterized in the acute form by the classical sequence of pain (dolor), heat (calor), redness (rubor), swelling (tumor), and loss of function (functio laesa). Histologically, it involves a complex series of events including dilation of the arterioles, capillaries, and venules with increased permeability and blood flow; exudation of fluids, including plasma proteins; and leukocytic migration into the inflammatory focus."

The inflammatory response is any response characterized by inflammation as defined above. It is well known to those skilled in the medical arts that the inflammatory response causes much of the physical discomfort, i.e., pain and loss of function, that has come to be associated with different diseases and injuries. Accordingly, it is a common medical practice to administer pharmacological agents which have the effect of neutralizing the inflammatory response. Agents having these properties are classified as anti-inflammatory drugs. Anti-inflammatory drugs are used for the treatment of a wide spectrum of disorders and the same drugs are often used to treat different diseases. Treatment with anti-inflammatory drugs is not for the disease but rather for the symptom, i.e., inflammation.

Corticosteroids represent the most widely used class of compounds for the treatment of the anti-inflammatory response. Proteolytic enzymes represent another class of compounds which are claimed to have anti-inflammatory effects. Hormones which directly or indirectly cause the adrenal cortex to produce and secrete steroids represent another class of anti-inflammatory compounds. A number of non-hormonal anti-inflammatory agents have been described. Examples of steroidal and non-steroidal anti-inflammatory agents are listed in the Physician's Desk Reference to Pharmaceuticals, Specialities, and Biologicals, 1979.

The natural and synthetic corticosteroid preparations cause a number of severe side effects including elevation of blood pressure, salt and water retention, and increased potassium and calcium excretion. Moreover, corticosteroids may mask the signs of infection and enhance dissemination of infectious microorganisms. These hormones are not considered safe for use in pregnant women, and long-term corticosteroid treatment has been associated with gastric hyperactivity and/or peptic ulcers. Treatment with these compounds may also aggravate diabetes mellitus, requiring higher doses of insulin, and psychotic disorders. Hormonal anti-inflammatory agents which are indirectly to increase the production of endogenous corticosteroids have the same potential for adverse side effects. The non-hormonal anti-inflammatory agents are synthetic biochemical compounds which can be toxic at high doses with a wide spectrum of undesirable side effects. Accordingly, in spite of the large number of anti-inflammatory agents that are currently available, there still exists a need for a safe, effective, anti-inflammatory product which is free of side effects and adverse reactions.

If a natural food product, such as milk for example, could be obtained having anti-inflammatory effects it would be an easily administerable, readily available, safe therapeutic composition.

It has been known in the prior art to produce milks having a variety of therapeutic effects. The present inventor for example has disclosed a milk containing antibodies to *Streptococcus mutans* which has dental caries inhibiting effects (Beck, British Pat. No. 1,505,513). The milk is obtained by immunizing a cow with *S. mutans* antigen in two stages and obtaining the therapeutic milk therefrom. The present inventor has also disclosed a milk having antiarthritic properties (co-pending U.S. Ser. No. 875,140 filed Feb. 6, 1978). Heinbach, U.S. Pat. No. 3,128,230, has described milk containing globulins of $\alpha, \beta$ and $\gamma$ components, by inocculating a cow with antigenic mixtures. Petersen (U.S. Pat. No. 3,376,198 and Canadian Pat. No. 587,849), Holm, U.S. application (published) Ser. No. 628,987 and Tunnak et al (British Pat. No. 1,211,876) have also described antibody-containing milks. None of the aforementioned references however disclose or suggest milk having anti-inflammatory properties.

SUMMARY OF THE INVENTION

It is therefore an object of the invention to provide an anti-inflammatory milk.

Another object of the invention is to provide a process for producing an anti-inflammatory milk.

A further object of the invention is to provide a method for treating inflammation in animals.

These and other objects of the invention which will hereinafter become more readily apparent have been attained by providing a method for treating inflammation in an animal which comprises:

administering to said animal milk collected from a bovid being maintained in an anti-inflammatory-factor producing state.

DETAILED DESCRIPTION OF THE PREFERRED EMBODIMENTS

The invention comprises a natural food product (milk) which has anti-inflammatory properties and a method for producing the same. The invention represents a significant advance in the state of the art of anti-inflammatory pharmacology because the product of this invention has no adverse side effects. Anti-inflammatory milk can be used to treat inflammation associated with any disease or injury in animals and humans without fear of side effects because it is a natural food product. Examples of human disease conditions which may be treated with anti-inflammatory milk include: rheumatoid arthritis; psoriatic arthritis; ankylosing spondylitis; acute and subacute bursitis; acute non-specific tendonitis; acute gouty arthritis; systemic lupus erythematosus; systemic dermatomyositis; acute rheumatic carditis; pemphigus; bullous dermatitis; hepetiformis; severe erythema; multiform exfoliative dermatitis, and cirrhosis, seasonal perennial rhinitis; bronchial asthma; contact dermatitis; etopic dermatitis; serum sickness; allergic conjunctivitis; keratitis; herpes zoster; opthalmicus iritis; diffuse uveitis, and choriditus; optic neuritis, and sympathetic opthalmia, symptomatic sarcoidosis, Loeffler's Syndrome, and berylliosis; hemolytic anemia; palliative management of neoplastic diseases including: leukemia, lymphomas, tuberculosis, and meningitis. It should be emphasized in this regard that the product of the invention does not treat the disease, but rather the symptom of the disease. Accordingly, the product is applicable for use in any disease or injury which exhibits inflammation as a symptom.

In the process of this invention, the bovid includes any milk-producing member of the genus Bos, preferably cows, sheep and goats, most preferably cows.

The invention is based on the discovery that when a bovid is brought to a specific state of immunization by means of periodic booster administrations of an antigen or a mixture of antigens, the bovid will produce milk which has the highly beneficial property of decreasing inflammatory conditions. The effect is caused by the presence of a factor in the milk, herein called "anti-inflammatory factor". The factor is not produced by all bovids that are immunized. The induction of immune sensitivity alone is insufficient to cause the appearance of anti-inflammatory factor in milk, as is shown by the fact that normal cow's milk does not contain this factor, even though cows have become sensitized against various antigens during normal immunization against cow diseases.

Furthermore, the factor is not always produced by bovids maintained in the immune state by booster injections. It is only in a specific hyperimmune state called herein "anti-inflammatory factor producing state" that the milk has the desired effects. This special state is only achieved by administering periodic boosters with sufficiently high doses of antigens or mixtures of antigens. These doses are herein called "anti-inflammatory-factor producing doses". The preferred dose range should be equal to or greater than 50% of the dosage necessary to cause primary sensitization of the bovid. Thus, there is a booster dosage threshold below which no factor is produced in the milk even though the cow may be in what is normally called an immune state. In order to achieve the anti-inflammatory factor producing state it is essential to test the bovid's milk after a first series of booster administrations. If the milk does not contain the factor, a second series of boosters of higher dosage has to be administered. This process is repeated until factor appears in the milk.

In summary the process comprises the following steps:

1. Antigen selection.
2. Sensitization of the bovid by primary immunization.
3. Testing the serum of the bovid to confirm sensitivity induction.
4. Administering boosters of appropriate dosage to induce and maintain an anti-inflammatory factor producing state.
5. Testing anti-inflammatory properties of milk.
6. Collecting milk from the bovid during the anti-inflammatory factor producing state.

Step 1

Any antigens or combination of antigens may be employed. The antigens can be bacterial, viral, cellular, or any other substances to which the immune system of a bovid will respond. The critical point in Step 1 is that the antigen must be capable of inducing a state of immune sensitivity in the cow. The antigen can be administered by any method which causes sensitization. Preferably polyvalent antigens are used.

Step 2

The preferred method of immunization is by intramuscular injection. However, other methods such as intravenous injection, intraperineal injection, oral administration, rectal suppository, etc. can be used, providing the dose is sufficient to induce sensitivity. The dosage is normally $1 \times 10^6$ cells to $1 \times 10^{20}$ cells, preferably $10^8$ cells to $10^{10}$ cells, most preferably $2 \times 10^8$ cells.

Step 3 is to determine whether or not the cow has become sensitive to the antigen. There are a number of methods known to those skilled in the art of immunology to test for sensitivity, (Methods in Immunology and Immuno-Chemistry, William, C. A., Chase, W. M. Academic Press, N.Y., London (vols. 1–5) (1977)). Examples of these include skin sensitivity tests, serum tests for the presence of antibodies to the stimulating antigens, and tests designed to evaluate the ability of immune cells from the host to respond to the antigen. The type of test employed will depend to a large extent on the nature of the antigen used. The preferred method is to use a polyvalent vaccine consisting of multiple bacterial species as the antigen and to test for the presence of agglutinating antibodies in the serum of the cow before and after challenge with the vaccine. The appearance of milk antibodies after immunization with the vaccine is indicative of sensitivity, and at this point it is possible to proceed to Step 4. The minimum dose of antigen necessary to induce sensitivity depends on the type of antigen used.

Step 4 involves the induction and maintenance of the anti-inflammatory factor producing state. Once a bovid has been shown to be sensitized, this state is induced by repeated booster administrations of an appropriate dosage at fixed time intervals. The spacing of the administration depends on the nature of the antigen. A two-week booster interval is optimal for polyvalent bacterial antigens. Moreover, the booster administrations must not induce a state of immune tolerance. This will cause the animal to pass from an anti-inflammatory factor producing state to a state of immune tolerance to the antigen in which case the animal will cease to produce the anti-inflammatory factor.

It might also be possible, for example, to use a combination of different immunization procedures, i.e., intramuscular injection for primary immunization and intravenous injection for booster injections, etc. Many different combinations of immunization methods might be employed by those skilled in the art to (1) sensitize and (2) induce the anti-inflammatory factor producing state.

Step 5 is to test the anti-inflammatory properties of the milk. The rat paw test is the standard animal test for anti-inflammatory drugs. ((1) Winter, C. A., Risley, G. A., Nuss, G. W., "Carrageenin-Induced Edema in the Hind Paw of the Rat as an Assay for Anti-inflammatory Drugs", Proc. Soc. Exp. Biol. Med. 3, 544–547 (1967)). A variety of other tests might be employed. ((2) Watnick, A. S., and Sabin, C., (1972) "The Effects of Clonixin and Bethamethasone on Adjuvant-Induced Arthritis and Experimental Allergic Encephalomyelitis in Rats"., Jap. J. Pharm. 22, 741–748.) However, the rat paw test is the most simple and direct test available, and has been shown to be highly satisfactory for all anti-inflammatory drugs. This test involves the injection of carrageenan in a small quantity into the foot pad of adult white rats. This is known to induce the inflammatory response. Within hours after treatment the inflammatory response causes the rat's foot to swell in size. The degree of swelling can be determined volumetrically and/or be determining the change in weight of the rat's paw. Anti-inflammatory drugs have the ability to block inflammation of the rat paw.

Step 6 involves collection and processing of the milk. The milk can be collected by conventional methods; however, special processing is necessary to protect the anti-inflammatory properties of the milk. The anti-inflammatory agent is heat sensitive. Accordingly, low temperature pasteurization is required. The pasteurization temperature should not exceed 140° C. Following pasteurization, the fat is removed by standard procedures and the milk is spray dried. Conventional spray-drying procedures are used with the exception that the milk is concentrated under vacuum at low temperature so as not to destroy the anti-inflammatory factor. (See eg. Kosikowski, F., "Cheese and Fermented Milk Products", 2d Ed, 1977). The final product is a milk powder which has anti-inflammatory properties.

Fluid milk can also be used of course, as well as concentrated milk products or a fraction of the milk containing the biologically active factor such as the acid whey fraction.

The milk of the invention can be provided in any amount which affects the decrease of inflammatory conditions in warm-blooded animals. Daily amounts of 1 ml to 10 liters based on fluid milk can be provided, depending on the particular circumstance of the inflammation and the animal species.

The fat-free milk can of course be incorporated into any food product as long as the food product is not treated at a temperature which is too elevated and would inactivate the anti-inflammatory properties of the product. A temperature lower than 150° C. is preferred. For example puddings or yogurt may be prepared with anti-inflammatory milk.

Further, when the fat free milk is treated with acid at about room temperature (bringing the pH of the milk to about 4.2–4.6) and the casein is separated after precipitation thereof, it is found that the acid whey supernatant fraction contains the anti-inflammatory factor. This acid whey fraction may also be added to syrups, ice-cream mixes, candy, beverages, cattle feeds or the like. (See Kosikowski, Supra, p 446).

Having now generally described this invention, the same will be further described by reference to certain specific examples which are provided herein for purposes of illustration only and are not intended to be limiting unless otherwise specified.

EXAMPLE 1

Five Holstein cows were immunized against Escherichia coli (American Type Culture Strain No. 13076). The primary immunization was accomplished by intramuscular injection of a vaccine containing heat-killed E. coli cells suspended in physiological saline. The concentration of bacterial cells was $4 \times 10^8$/cc. A dose of 5 cc ($20 \times 10^8$) cells was injected i.m. once weekly for four consecutive weeks. Milk collected during the fifth week was tested for the presence of antibodies against E. coli. The presence of antibody against E. coli was determined using a micro-agglutination procedure. This procedure involves reacting different dilutions of milk whey with a fixed concentration of E. coli bacterial cells suspended in buffer. The presence of antibodies in the milk causes agglutination of the bacterial cells. The milk is diluted in a serial fashion and there comes a point when the concentration of antibodies is too low to cause the agglutination reaction. The maximum dilution which causes agglutination is the antibody titer. The presence of high antibody concentration in milk is an indication that the immunization procedure causes sensitization of the cow's immune system against the antigen. Table 1 compares the antibody titer against E. coli in the five cows before and after primary immunization.

TABLE 1

Milk Antibody Titer in 5 Cows Before and After Immunization Against E. coli

| Cow No. | Before Immunization | After Immunization |
|---|---|---|
| 1 | 0 | 640 |
| 2 | 0 | 1280 |
| 3 | 0 | 5000 |
| 4 | 0 | 1280 |
| 5 | 0 | 10,000 |

In each case there was a significant increase in the milk titer against E. coli following immunization. From this we conclude that the immunization caused sensitization of the cow against the E. coli. Having induced a state of sensitivity, the cows were given booster injections of the same dose of antigen every 14 days, thus establishing and maintaining a period of anti-inflammatory factor producing state during which time the milk was collected daily and processed to obtain anti-inflammatory skimmed powdered milk.

The anti-inflammatory skimmed powdered milk induced by the method outlined above was tested for anti-inflammatory properties using the rat paw test.

Ten adult white rats were fed 10 mg. of anti-inflammatory milk suspended in 20 cc of $H_2O$ daily for five consecutive days. On the fifth day the right rat paw was injected with 1/10 of a cc of 1% carrageenan saline solution, and 24 hours after injection the rats were sacrificed and the right and left paws amputated and weighed. The mean weight of the left paw in the experimental group was compared to the mean weight of the right paw using the student's paired T test to determine if a statistically significant difference exists between right and left paws. The identical experiment was conducted in a second group of rats using the same quantity of normal skimmed milk instead of the anti-inflammatory milk. A third group of rats was fed just water. Results from this experiment are summarized in Table 2.

TABLE 2

| Rat No. | Rat Paw Test Results - Example 1 | | |
|---|---|---|---|
| | Right Paw Wt. (g) | Left Paw Wt. (g) | Difference |
| | Group 1 - Fed Anti-Inflammatory Milk | | |
| 1 | 1.87 | 1.66 | 0.21 |
| 2 | 1.61 | 1.61 | 0.00 |
| 3 | 1.68 | 1.65 | 0.03 |
| 4 | 1.95 | 1.87 | 0.08 |
| 5 | 1.82 | 1.77 | 0.05 |
| 6 | 1.83 | 1.74 | 0.09 |
| 7 | 1.84 | 1.67 | 0.17 |
| 8 | 1.63 | 1.68 | 0.05 |
| 9 | 1.75 | 1.70 | 0.05 |
| 10 | 1.78 | 1.78 | 0.00 |
| Mean ± S.D. | 1.78 ± 0.11 | 1.71 ± 0.08 | 0.07 ± 0.07 |
| | Group 2 - Fed Normal Milk | | |
| 1 | 1.68 | 1.48 | 0.20 |
| 2 | 1.82 | 1.67 | 0.15 |
| 3 | 1.69 | 1.60 | 0.09 |
| 4 | 1.95 | 1.69 | 0.26 |
| 5 | 1.96 | 1.74 | 0.22 |
| 6 | 2.22 | 1.77 | 0.45 |
| 7 | 1.78 | 1.49 | 0.29 |
| 8 | 1.75 | 1.60 | 0.15 |

TABLE 2-continued

Rat Paw Test Results - Example 1

| Rat No. | Right Paw Wt. (g) | Left Paw Wt. (g) | Difference |
|---|---|---|---|
| 9 | 1.78 | 1.70 | 0.08 |
| 10 | 2.12 | 1.61 | 0.51 |
| Mean ± S.D | 1.88 ± 0.18 | 1.64 ± 0.10 | 0.24 ± 0.14 |
| Group 3 - Fed Water | | | |
| 1 | 1.80 | 1.48 | 0.32 |
| 2 | 1.78 | 1.55 | 0.23 |
| 3 | 1.75 | 1.63 | 0.12 |
| 4 | 1.89 | 1.67 | 0.22 |
| 5 | 2.02 | 1.77 | 0.25 |
| 6 | 1.95 | 1.73 | 0.22 |
| 7 | 1.78 | 1.65 | 0.13 |
| 8 | 1.87 | 1.60 | 0.27 |
| 9 | 1.88 | 1.62 | 0.26 |
| 10 | 1.90 | 1.77 | 0.13 |
| Mean ± S.D. | 1.86 ± 0.09 | 1.65 ± 0.09 | 0.22 ± 0.07 |

The mean weight of the right hind paw in rats fed $H_2O$ was significantly greater than the mean weight of the left paw due to swelling produced in the right paw by the injection of carrageenan. The identical result occurred in the group of rats that were fed normal powdered skimmed mild, whereas in rats fed anti-inflammatory skimmed powdered milk, there was no significant difference between the mean weight of the right and left paws. These results clearly demonstrate that the product of the invention blocks the inflammatory response.

COMPARATIVE EXAMPLE 1

The process of Example 1 was repeated except that the dosage of *E. coli* cells used for booster injections was $1 \times 10^3$. The cow was in an immune state but not in an anti-inflammatory factor producing state, as demonstrated by antibodies in the milk against *E. coli* and by the non-effectiveness of the milk obtained therefrom to block rat paw inflammation.

EXAMPLE 2

The identical experiment as described in Example 1 was repeated using the same dosage but utilizing a different bacterial species, i.e., *Salmonella enteritidis*, as the selected antigen for the induction of the sensitivity. The results of the anti-inflammatory tests performed on the milk produced using this antigen were positive.

EXAMPLE 3

The identical experiment as described in Example 1 was undertaken with the exception that a polyvalent vaccine comprised of the bacterial strains listed below in Table 3 was used as the selected antigen. The different bacterial strains were combined by mixing equal weights of the lyophilized bacterial cells and diluting the mixture in saline to obtain a concentration identical to that used in Example 1. Results of the anti-inflammatory tests on milk produced using this selected antigen were positive.

TABLE 3

| Bacterial Antigens | |
|---|---|
| ORGANISM | *ATTC NO. |
| *Staphylococcus aureus* | 11631 |
| *Staphylococcus epidermidis* | 155 |
| *Streptococcus pyogenes*, A. Type 1 | 8671 |
| *Streptococcus pyogenes*, A. Type 3 | 10389 |
| *Streptococcus pyogenes*, A. Type 5 | 12347 |
| *streptococcus pyogenes*, A. Type 8 | 12389 |
| *Streptococcus pyogenes*, A. Type 12 | 11434 |

TABLE 3-continued

| Bacterial Antigens | |
|---|---|
| ORGANISM | *ATTC NO. |
| *Streptococcus pyogenes*, A. Type 14 | 12972 |
| *Streptococcus pyogenes*, A. Type 18 | 12357 |
| *Streptococcus pyogenes*, A. Type 22 | 10403 |
| *Aerobacter aerogenes* | 884 |
| *Escherichia coli* | 26 |
| *Salmonella enteritidis* | 13076 |
| *Pweudomonas aeruginosa* | 7700 |
| *Klebsiella pneumoniae* | 9590 |
| *Salmonella typhimurium* | 13311 |
| *Haemophilus influenzae* | 9333 |
| *Streptococcus viridans* | 6249 |
| *Proteus vulgaris* | 13315 |
| *Shigella dysenteriae* | 11835 |
| Streptococcus, Group B | |
| Diplococcus pneumoniae | |
| Streptococcus mutans | |
| Corynebacterium, Acne, Types 1 & 2 | |

*American Type Culture Collection 12301 Parklawn Drive Rockville, Maryland 20852

It should be noted here that the milk produced in this Example is identical to that produced in a preferred embodiment of the invention disclosed in copending U.S. application Ser. No. 875,140, filed Feb. 6, 1978 by the present inventor. This co-pending application discloses that the milk of the present Example also has highly beneficial anti-arthritic properties. The anti-arthritic properties of the milk are due to the presence of antibodies therein which decrease the levels of Rheumatoid Factor (RF) in the blood of arthritic patients. It is of course possible that the antibodies present in the milk and the anti-inflammatory factor of the same milk, act in a synergistic manner. The factor may decrease joint inflammation while the antibodies may decrease the level of RF.

It must be noted however that (a) antibody isolated from this milk has no anti-inflammatory effects; (b) non-arthritic conditions such as allergies or tennis elbow can be successfully treated with the milk; (c) there is no mechanism to explain how an anti-inflammatory factor can decrease the level of RF in the blood. These facts indicate that the anti-inflammatory and anti-arthritic properties of the milk are caused by different factors, and that anti-inflammatory factor is not an antibody.

EXAMPLE 4

The identical experiment was undertaken as per Example 1 with the exception that a protein hormone (hCG) was used in lieu of bacterial cells as the selected antigen. For this experiment 10 mg of chorionic gonadotropin hormone was dissolved in 5 mls of physiological saline to formulate the vaccine used for both primary immunization and subsequent booster immunizations according to the same sequence as described for Example 1. The results from anti-inflammatory tests on the milk produced using this selected antigen were positive.

EXAMPLE 5

The identical procedure as per Example 1 was performed with the exception that an animal cell antigen was used in lieu of the bacterial antigen for sensitization of the cow and subsequent booster injections. For this experiment, 10 mg of rat mammary tumor tissue was used to prepare the vaccine for the primary and booster injections. The vaccine was prepared by homogenizing 10 mg of tumor tissue obtained from mammary tumors collected from rats. The tumors were thoroughly homogeneized and the resulting material was injected into cows using the same primary and booster immunization schedule as described in Example 1. The results of the anti-inflammatory tests in milk produced using this selected antigen for the induction of sensitivity and maintenance of the hyperimmune state were positive.

EXAMPLE 6

A strain of *Streptococcus mutans* was cultured in accordance with established techniques. Cultures of *S. mutans* AHT (serological group a), BHT (group b), 10449 (group C) and 6715 (group d) were grown in dialyzed tryptose medium. The cells were harvested by centrifugation at 4000 X G and washed five times with 0.1 M phosphate buffered saline, pH 7.0. The cells were inactivated by heating at 60° C. for 30 minutes and resuspended to a final concentration of *S. mutans* AHT, BHT, 10449 and 6715 at $5 \times 10^8$ cells/ml. This preparation was used to immunize two cows. Each cow was immunized on two separate occasions with fresh antigen from all four groups of *S. mutans* (groups a, b, c and d). A cow was then immunized in accordance with the established techniques of this invention to generate a milk product. Following immunization, blood samples of the cow were taken until the serum antibody titre reached its highest lever, then the milk was collected. The milk itself was then dried and powdered, again in accordance with established techniques to produce a powdered milk having positive anti-inflammatory effects.

It should be noted here that the milk produced in this Example is identical to the caries-inhibiting milk disclosed by Beck (the present inventor) in British Pat. No. 1,505,513.

Conclusions

The preceding examples establish an important principle of the invention; i.e., that the nature of the antigen used to induce sensitivity and to maintain the anti-inflammatory factor producing state can be varied. Although it is possible to maintain an anti-inflammatory factor producing state utilizing a single antigen as demonstrated in Examples 1 and 2, the likelihood of tolerance developing through the use of a single antigen is much greater than that of multiple antigens as per Example 3. The same rationale would apply to antigens of different types including hormones, viruses, proteins, toxins, or the like.

Having now generally described this invention it will become readily apparent to one skilled in the art that many changes and modifications can be made thereto without affecting the spirit or scope thereof.

What is claimed as new and desired to be secured by Letters Patent of the United States is:

1. A method of treating inflammation in an animal which comprises administering to said animal an anti-inflammatory effective amount of milk collected from a bovid being maintained in an anti-inflammatory factor producing state; wherein said inflammation is caused by a condition selected from the group consisting of acute and subacute bursitis, acute non-specific tendonitis, systemic lupus erythematosus, systemic dermatomyositis, acute rheumatic carditis, pemphigus, bullous dermatitis, hepetiformis, severe erythema, multiform exfoliative dermatitis, cirrhosis, seasonal perennial rhinitis, bronchial asthma, etopic dermatitis, serum sickness, keratitis, opthalmicus iritis, diffuse ureitis, choriditis, optic neuritis, sympathetic opthalmia, symptomatic sarcoidosis, Loeffler's Syndrome, berylliosis and hemolytic anemia.

2. The method of claim 1 wherein said milk is in powdery form.

3. The method of claim 1 wherein said milk is in fluid form.

4. The method of claim 1 wherein said milk is in concentrated form.

5. The method of claim 1 wherein said milk is incorporated into a food product.

6. The method of claim 5 wherein said product is yogurt.

7. The method of claim 1 wherein said bovid is a cow.

8. The method of claim 1 wherein said bovid is maintained in said anti-inflammatory factor producing state by administering to said bovid booster injections of an antigen or mixture of antigens.

9. The method of claim 8 wherein said antigen or mixture of antigens booster is injected in a dose of $10^6$ cells to $10^{20}$ cells.

10. The method of claim 1 wherein said milk is prepared by a process which comprises:
sensitizing a bovid with an antigen or mixture of antigens;
administering boosters of antigen of a dosage sufficient to induce and maintain an anti-inflammatory producing state in said bovid; and thereafter collecting said milk from said bovid.

11. The method of claim 10 wherein said process further comprises:
pasteurizing said collected milk; and
removing the fat from said milk.

12. The method of claim 5 wherein said food product is a syrup.

13. The method of claim 5 wherein said food product is an ice-cream mix.

14. The method of claim 5 wherein said food product is a candy.

15. The method of claim 5 wherein said food product is a beverage.

16. The method of claim 5 wherein said food product is a cattle feed.

* * * * *